United States Patent
Ross et al.

[19]

[11] Patent Number: 5,883,125
[45] Date of Patent: Mar. 16, 1999

[54] BENZYLOXY SUBSTITUTED AROMATICS AND THEIR USE AS FUNGICIDES AND INSECTICIDES

[75] Inventors: Ronald Ross, Jamison; Ted Tsutomu Fujimoto, Churchville; Steven Howard Shaber, Horsham, all of Pa.

[73] Assignee: Rohm and Haas Company, Philadelphia, Pa.

[21] Appl. No.: 857,375

[22] Filed: Jun. 2, 1997

Related U.S. Application Data

[60] Provisional application No. 60/019,230 Jun. 6, 1996.
[51] Int. Cl.⁶ .................................................. A01N 37/10
[52] U.S. Cl. ..................... 514/545; 514/256; 514/354; 514/355; 514/357; 514/448; 514/539; 514/620; 514/621; 546/314; 546/315; 548/333.5; 548/334.1; 549/72; 560/35; 560/51; 560/52; 560/53; 564/165; 564/169
[58] Field of Search ................... 560/51, 52, 53, 560/35; 514/545, 256, 354, 355, 357, 448, 539, 620, 621; 564/165, 169, 314, 315; 548/333.5, 334.1; 549/72

[56] References Cited

U.S. PATENT DOCUMENTS

| | | |
|---|---|---|
| 4,914,128 | 4/1990 | Schirmer et al. . |
| 5,021,581 | 6/1991 | Clough et al. . |
| 5,145,980 | 9/1992 | Wenderoth et al. . |
| 5,185,342 | 2/1993 | Hayase et al. . |
| 5,315,025 | 5/1994 | Bushell et al. . |
| 5,356,931 | 10/1994 | Kirstgen et al. ............... 514/478 |
| 5,389,619 | 2/1995 | Doetzer et al. ............... 514/63 |
| 5,395,854 | 3/1995 | Brand et al. . |
| 5,438,059 | 8/1995 | Clough et al. . |

FOREIGN PATENT DOCUMENTS

| | | |
|---|---|---|
| 0278595 A2 | 8/1988 | European Pat. Off. . |
| 0398692 A2 | 11/1990 | European Pat. Off. . |
| 0477631 A1 | 4/1992 | European Pat. Off. . |
| 0628540 A1 | 12/1994 | European Pat. Off. . |
| 0673923 A1 | 9/1995 | European Pat. Off. . |

*Primary Examiner*—Brian M. Burn
*Attorney, Agent, or Firm*—Guy T. Donatiello

[57] ABSTRACT

Compounds with fungicidal and insecticidal properties having formula I

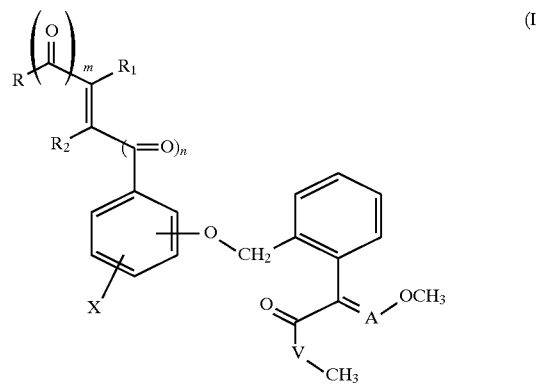

wherein A is N or CH; V is O or NH;

m and n are integers 0 and 1 provided that m+n is 1;

X is independently selected from hydrogen, halo, $(C_1-C_4)$ alkyl, and $(C_1-C_4)$ alkoxy;

R is independently selected from, $(C_1-C_{12})$alkyl, halo $(C_1-C_{12})$alkyl, $(C_2-C_8)$ alkenyl, $(C_2-C_8)$alkynyl, $(C_1-C_{12})$alkoxy$(C_1-C_{12})$alkyl, $(C_3-C_7)$ cycloalkyl, $(C_3-C_7)$cycloalkyl$(C_1-C_4)$alkyl, aryl, aralkyl, and heterocyclic moieties;

R is independently selected from $(C_1-C_{12})$alkyl, halo $(C_1-C_{12})$alkyl, $(C_2-C_8)$ alkenyl, $(C_2-C_8)$alkynyl, $(C_1-C_{12})$alkoxy$(C_1-C_{12})$alkyl, $(C_3-C_7)$ cycloalkyl, $(C_3-C_7)$cycloalkyl$(C_1-C_4)$alkyl, aryl, aralkyl, and heterocyclic;

$R_1$ and $R_2$ are independently selected from hydrogen, $(C_1-C_6)$alkyl, halo$(C_1-C_{12})$ alkyl, $(C_3-C_7)$cycloalkyl, $(C_3-C_7)$cycloalkyl$(C_1-C_4)$alkyl, cyano, carboxy $(C_1-C_4)$alkyl, and aryl; provided at least one of $R_1$ and $R_2$ is H.

19 Claims, No Drawings

BENZYLOXY SUBSTITUTED AROMATICS AND THEIR USE AS FUNGICIDES AND INSECTICIDES

This is a nonprovisional application of prior provisional application Ser. No. 60/019,230 filed Jun. 6, 1996.

The present invention relates to benzyloxy substituted-phenyl compounds, compositions containing these compounds and methods for controlling fungi and insects by the use of a fungitoxic and insecticidal amount of these compounds.

It is known that propenoic acids and oxime ethers of certain benzyloxy substituted phenyl compounds are useful as fungicides. The substitution of the phenyl ring is known in the art (see for example U.S. Pat. No. 5,185,342).

We have discovered phenyl derivatives which possess an acyl substituent to which is bonded an unsaturated group or an unsaturated group to which is bonded an acyl group. These novel compositions also possess fungicidal and insecticidal properties.

The novel benzyloxy substitutedphenyl compounds of the present invention have the Formula (I)

wherein A is N or CH; V is O or NH;
m and n are integers 0 and 1, provided that m+n is 1;
X is independently selected from hydrogen, halo, $(C_1-C_4)$ alkyl, and $(C_1-C_4)$ alkoxy;
R is independently selected from $(C_1-C_{12})$alkyl, halo $(C_1-C_{12})$alkyl, $(C_2-C_8)$ alkenyl, $(C_2-C_8)$alkynyl, $(C_1-C_{12})$alkoxy$(C_1-C_{12})$alkyl, $(C_3-C_7)$ cycloalkyl, $(C_3-C_7)$cycloalkyl$(C_1-C_4)$alkyl, aryl, aralkyl, and heterocyclic;
$R_1$ and $R_2$ are independently selected from hydrogen, $(C_1-C_6)$alkyl, halo$(C_1-C_6)$ alkyl, $(C_3-C_7)$cycloalkyl, $(C_3-C_7)$cycloalkyl$(C_1-C_4)$alkyl, cyano, carboxy $(C_1-C_4)$alkyl and aryl;
provided that at least one of $R_1$ and $R_2$ must be hydrogen.

The aforementioned $(C_1-C_{12})$alkyl, $(C_2-C_8)$alkenyl, $(C_2-C_8)$alkynyl and $(C_3-C_7)$cycloalkyl groups may be optionally substituted with up to three substituents selected from the group consisting of halogen, nitro, trihalomethyl and cyano.

The term alkyl includes both branched and straight chained alkyl groups from 1 to 12 carbon atoms. Typical alkyl groups are methyl, ethyl, n-propyl, isopropyl, n-butyl, sec-butyl, isobutyl,t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

The term alkenyl refers to an ethylenically unsaturated hydrocarbon group, straight or branched, having a chain length of 2 to 12 carbon atoms and 1 or 2 ethylenic bonds.

The term haloalkenyl refers to an alkenyl group substitued with 1 to 3 halogen atoms. The term alkynyl refers to an unsaturated hydrocarbon group, straight or branched, having a chain length of 2 to 12 carbon atoms and 1 or 2 acetylenic bonds.

The term cycloalkyl refers to a saturated ring system having 3 to 7 carbon atoms.

The term aryl is understood to be phenyl or napthyl, which maybe further substituted with up to three substituents selected from the group consisting of halogen, cyano, nitro, trihalomethyl, phenyl, phenoxy, $(C_1-C_4)$alkyl, $(C_1-C_4)$ alkylthio, $(C_1-C_4)$alkylsulfoxide $(C_1-C_6)$alkoxy and halo$(C_1-C_4)$alkyl.

Typical aryl substituents include but are not limited to 4-chlorophenyl, 4-fluoro-phenyl, 4-bromophenyl, 2-methoxyphenyl, 2-methylphenyl, 3-methyphenyl, 4-methyl-phenyl, 2,4-dibromophenyl, 3,5-difluorophenyl, 2,4,6-trichlorophenyl, 4-methoxy-phenyl, 2-chloronapthyl, 2,4-dimethoxyphenyl, 4-(trifluoromethyl)phenyl and 2-iodo-4-methylphenyl.

The term heterocyclic refers to a substituted or unsubstituted 5 or 6 membered unsaturated ring containing one, two or three heteroatoms, preferably one or two heteroatoms selected from oxygen, nitrogen and sulfur; or is a bicyclic unsaturated ring system containing up to 10 atoms including one heteratom selected from oxygen, nitrogen and sulfur. Examples of heterocycles includes, but is not limited to, 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents independently selected from $(C_1-C_4)$alkyl, halogen, cyano, nitro and trihalomethyl.

The term aralkyl is used to describe a group wherein the the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chlorophenyl)ethyl, 2-(3-chlorophenyl)ethyl, 2-(4-chlorophenyl) ethyl, 2-(2-fluorophenyl)- ethyl, 2-(3-fluorophenyl)ethyl, 2-(4-fluorophenyl)ethyl, 2-(2-methylphenyl)ethyl, 2-(3-methylphenyl)ethyl, 2-(4-methylphenyl)ethyl, 2-(4-trifluoromethylphenyl)ethyl, 2-(2-methoxyphenyl)ethyl, 2-(3-methoxyphenyl)ethyl, 2-(4-methoxyphenyl)ethyl, 2-(2,4-dichlorophenyl)ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichlorophenyl)propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)ethyl, 3-(2-methoxyphenyl)propyl, 3-(3-methoxyphenyl)propyl, 3-(4-methoxyphenyl)propyl, 3-(4-trifluoromethyl-phenyl)propyl, 3-(2,4-dichlorophenyl)propyl and 3-(3,5-dimethoxyphenyl) propyl.

Typical phenbutyl moieties include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl) butyl, 4-(3-methylphenyl)-butyl, 4-(4-methylphenyl)butyl, 4-(2,4-dichlorophenyl)butyl, 4-(2-methoxphenyl)butyl, 4-(3-methoxyphenyl)butyl and 4-(4-methoxyphenyl)butyl.

Halogen or halo is defined as iodo, fluoro, bromo and chloro moieties.

Those skilled in the art will recognize the double bond between $R_1$ and $R_2$ can exist as cis or trans isomers. These isomers can be separated into individual components by conventional means. Both the individual isomeric compounds and mixtures thereof form subjects of the invention and have fungicidal properties.

The C=C or C=N double bond substituents of the benzyloxy fragment in the novel compounds of the general Formula I may be obtained in preparation as E/Z isomeric mixtures. These isomers can be separated into individual components by conventional means. Both the individual isomeric compounds and mixtures thereof form subjects of the invention and have fungicidal properties.

The present invention also includes the enantiomorphs, salts and complexes of Formula (I).

As used throughout this invention the structures are defined to include the cis/trans and E/Z isomeric mixtures.

A preferred embodiment of this invention are the compounds, enantiomorphs, salts and complexes of Formula (I) is when $R_1$ and $R_2$ are hydrogen and R is $(C_1-C_{12})$alkyl, phenyl substituted with preferably one or two substituents independently selected from halo, trihalomethyl, cyano, $(C_1-C_4)$alkyl, $(C_1-C_4)$ alkylthio, $(C_1-C_4)$alkoxy or phenyl, and where the $OCH_2$(2-substitutedphenyl) is bonded at the meta position to the $(C=O)_n$-C=C-$(C=O)_m$-R substituent of the phenyl ring as shown below. R, n and m as used here are the same as defined above.

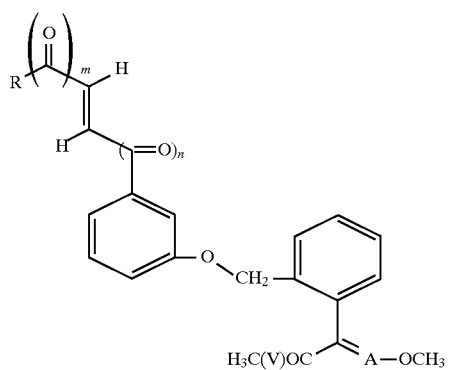

A more preferred embodiment of this invention are the compounds, enatiamorphs, salts and complexes of Formula (I) is when $R_1$, $R_2$ and X are hydrogen, R is t-butyl, n-propyl, halophenyl and A is CH and V is O. The preferred geometry when A is CH or N is the E isomer.

Typical compounds encompassed by the present invention of Formula I include those compounds presented in Table 1 of Formula II, III and IV.

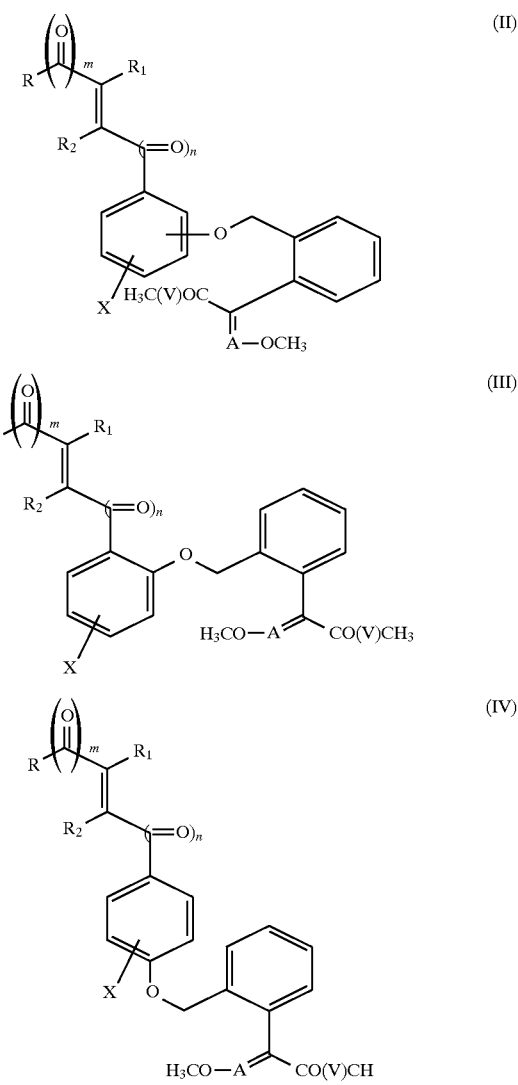

where $R_1$ and $R_2$=H and the other substituents are defined in the table below.

TABLE 1

| Cmpd # | R | Formula | n | m | X | A | V |
|---|---|---|---|---|---|---|---|
| 1.01 | Ar | II | 0 | 1 | H | CH | O |
| 1.02 | Ar | III | 0 | 1 | H | CH | O |
| 1.03 | Ar | IV | 0 | 1 | H | CH | O |
| 1.04 | 2-Cl(Ar) | II | 0 | 1 | H | CH | O |
| 1.05 | 2-Cl(Ar) | III | 0 | 1 | H | CH | O |
| 1.06 | 2-Cl(Ar) | IV | 0 | 1 | H | CH | O |
| 1.07 | 3-Cl(Ar) | II | 0 | 1 | H | CH | O |
| 1.08 | 3-Cl(Ar) | III | 0 | 1 | H | CH | O |
| 1.09 | 3-Cl(Ar) | IV | 0 | 1 | H | CH | O |
| 1.10 | 4-Cl(Ar) | II | 0 | 1 | H | CH | O |
| 1.11 | 4-Cl(Ar) | III | 0 | 1 | H | CH | O |
| 1.12 | 4-Cl(Ar) | IV | 0 | 1 | H | CH | O |
| 1.13 | 2-Br(Ar) | II | 0 | 1 | H | CH | O |
| 1.14 | 3-Br(Ar) | II | 0 | 1 | H | CH | O |
| 1.15 | 4-Br(Ar) | II | 0 | 1 | H | CH | O |
| 1.16 | 2-F(Ar) | II | 0 | 1 | H | CH | O |
| 1.17 | 3-F(Ar) | II | 0 | 1 | H | CH | O |
| 1.18 | 4-F(Ar) | II | 0 | 1 | H | CH | O |
| 1.19 | 2-OCH$_3$(Ar) | II | 0 | 1 | H | CH | O |
| 1.20 | 3-OCH$_3$(Ar) | II | 0 | 1 | H | CH | O |
| 1.21 | 4-OCH$_3$(Ar) | II | 0 | 1 | H | CH | O |
| 1.22 | 2-CH$_3$(Ar) | II | 0 | 1 | H | CH | O |

TABLE 1-continued

| Cmpd # | R | Formula | n | m | X | A | V |
|---|---|---|---|---|---|---|---|
| 1.23 | 3-$CH_3$(Ar) | II | 0 | 1 | H | CH | O |
| 1.24 | 4-$CH_3$(Ar) | II | 0 | 1 | H | CH | O |
| 1.25 | 2-$CF_3$(Ar) | II | 0 | 1 | H | CH | O |
| 1.26 | 3-$CF_3$(Ar) | II | 0 | 1 | H | CH | O |
| 1.27 | 4-CF3(Ar) | II | 0 | 1 | H | CH | O |
| 1.28 | 2-$NO_2$(Ar) | II | 0 | 1 | H | CH | O |
| 1.29 | 3-$NO_2$(Ar) | II | 0 | 1 | H | CH | O |
| 1.30 | 4-$NO_2$(Ar) | II | 0 | 1 | H | CH | O |
| 1.31 | 2,4-Cl(Ar) | II | 0 | 1 | H | CH | O |
| 1.32 | 2,5-Cl(Ar) | II | 0 | 1 | H | CH | O |
| 1.33 | 2,4-F(Ar) | II | 0 | 1 | H | CH | O |
| 1.34 | 2,5-F(Ar) | II | 0 | 1 | H | CH | O |
| 1.35 | 3,4-F(Ar) | II | 0 | 1 | H | CH | O |
| 1.36 | $CH_3$ | II | 0 | 1 | H | CH | O |
| 1.37 | $CH_2CH_3$ | II | 0 | 1 | H | CH | O |
| 1.38 | $CH_2CH_2CH_3$ | II | 0 | 1 | H | CH | O |
| 1.39 | $CH(CH_3)_2$ | II | 0 | 1 | H | CH | O |
| 1.40 | $CH_2(CH_2)_3CH_3$ | II | 0 | 1 | H | CH | O |
| 1.41 | $CH_2(CH_2)_4CH_3$ | II | 0 | 1 | H | CH | O |
| 1.42 | $CH_2CH(CH_3)_2$ | II | 0 | 1 | H | CH | O |
| 1.43 | $CH(CH_3)CH_2CH_3$ | II | 0 | 1 | H | CH | O |
| 1.44 | $C(CH_3)_3$ | II | 0 | 1 | H | CH | O |
| 1.45 | $CH_2C(CH_3)_3$ | II | 0 | 1 | H | CH | O |
| 1.46 | $CH(CH_3)CH_2CH_2CH_3$ | II | 0 | 1 | H | CH | O |
| 1.47 | $C(CH3)_2CH_2CH_3$ | II | 0 | 1 | H | CH | O |
| 1.48 | $CF_3$ | II | 0 | 1 | H | CH | O |
| 1.49 | $CF_2CF_3$ | II | 0 | 1 | H | CH | O |
| 1.50 | $CH_2CF_3$ | II | 0 | 1 | H | CH | O |
| 1.51 | $CH=CH_2$ | II | 0 | 1 | H | CH | O |
| 1.52 | cyclopropyl | II | 0 | 1 | H | CH | O |
| 1.53 | cyclopentyl | II | 0 | 1 | H | CH | O |
| 1.54 | cyclohexyl | II | 0 | 1 | H | CH | O |
| 1.55 | $CH_2OCH_3$ | II | 0 | 1 | H | CH | O |
| 1.56 | $CH_2OCH_2CH_3$ | II | 0 | 1 | H | CH | O |
| 1.57 | $CH_2CH_2OCOAr$ | II | 0 | 1 | H | CH | O |
| 1.58 | $CH_2OCH_2Ar$ | II | 0 | 1 | H | CH | O |
| 1.59 | 2-pyridyl | II | 0 | 1 | H | CH | O |
| 1.60 | 3-pyridyl | II | 0 | 1 | H | CH | O |
| 1.61 | 2-pyrimidyl | II | 0 | 1 | H | CH | O |
| 1.62 | 4-pyrimidyl | II | 0 | 1 | H | CH | O |
| 1.63 | 2-thienyl | II | 0 | 1 | H | CH | O |
| 1.64 | 3-thienyl | II | 0 | 1 | H | CH | O |
| 1.65 | 2-naphthyl | II | 0 | 1 | H | CH | O |

Further typical compounds described by the present invention are described in the following tables.

Table 2

Compounds 2.1 to 2.65 are Compounds of Table 1 of Formula II, III, IV where in n=1 and m=0, $R_1$ and $R_2$ are H and V=O and A is CH.

Table 3

Compounds 3.1 to 3.65 are Compounds of Table 1 of Formula II, III, IV where in n=0 and m=1, $R_1$ and $R_2$ are H and V=O and A is N.

Table 4

Compounds 4.1 to 4.65 are Compounds of Table 1 of Formula II, III, IV where in n=1 and m=0, $R_1$ and $R_2$ are H and V=O and A is N.

Table 5

Compounds 5.1 to 5.65 are Compounds of Table 1 of Formula II, III, IV where in n=0 and m=1, $R_1$ and $R_2$ are H and V=NH and A is N.

Table 6

Compounds 6.1 to 6.65 are Compounds of Table 1 of Formula II, III, IV where in n=1 and m=0, $R_1$ and $R_2$ are H and V=NH and A is N.

Table 7

Compounds 7.1 to 7.65 are Compounds of Table 1 of Formula II, III, IV where in n=0 and m=1, $R_1$=$CH_3$ and $R_2$=H and V=O and A is CH.

Table 8

Compounds 8.1 to 8.65 are Compounds of Table 1 of Formula II, III, IV where in n=0 and m=1, $R_1$=$CH_3$ and $R_2$=H and V=O and A is N.

Table 9

Compounds 9.1 to 9.65 are Compounds of Table 1 of Formula II, III, IV where in n=0 and m=1, $R_1$=$CH_3$ and $R_2$=H and V=NH and A is N.

Table 10

Compounds 10.1 to 10.65 are Compounds of Table 1 of Formula II, III, IV where in n=1 and m=0, $R_1$=H and $R_2$=$CH_3$ and V=O and A is CH.

Table 11

Compounds 11.1 to 11.65 are Compounds of Table 1 of Formula II, II, IV where in n=1 and m=0, $R_1$=H and $R_2$=$CH_3$ and V=O and A is N.

Table 12

Compounds 12.1 to 12.65 are Compounds of Table 1 of Formula II, III, IV where in n=1 and m=0, $R_1$=H and $R_2$=$CH_3$ and V=NH and A is N.

As used in Tables 1 to 12 Ar is understood to be phenyl.

The compounds of Formula I are prepared in a two step sequence. Scheme A describes the preparation of compounds of the formula (I) where n=0 and m=1. The α,β unsaturated compounds (V) can be prepared by conventional condensation techniques. For example *Organic Reactions,* Volume 16, describes the general aldol condensation and specifically the condensation of benzaldehydes with ketones. A hydroxybenzaldehyde is condensed with a ketone, $RCOCH_2R_1$, which when $R_1$=H a methyl ketone, provides the unsaturated intermediate V'.

Scheme A:

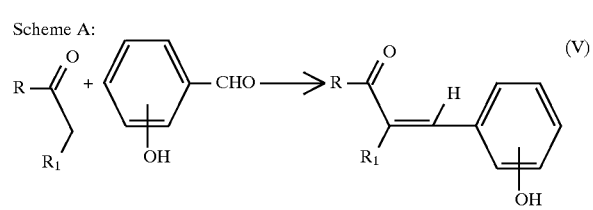

when $R_1$ = H provides the following reaction:

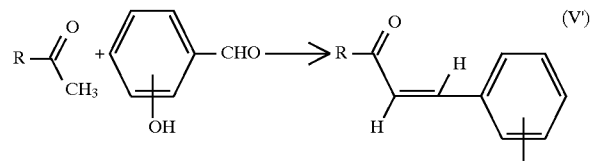

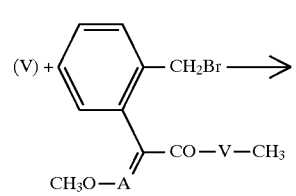

V = O or NH
A = CH or N

Scheme A:
-continued

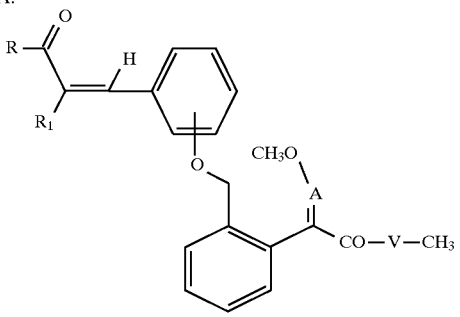

Substituted hydroxybenzaldehyde such as ortho, meta or para-hydroxybenzaldehyde provides three regioisomeric intermediates V and V'. A variety of reaction conditions can be employed to prepare the enones (V and V') which are described in *Organic Reactions,* Volume 16, pp. 69–85. For example, a ketone is dissolved in a hydroxylic solvent, such as ethanol, to which is added dropwise a solution of the hydroxybenzaldehyde in an aqueous basic solution. The bases used can be alkali metal hydroxides, such as potassium or sodium hydroxide and the dropwise addition is conducted from 0° C. to 35° C. preferably at ambient temperature.

Compounds of formula (VI) are prepared by the alkylation of intermediate V and V' with the appropriately substituted benzyl bromides. Alkylation of intermediate V' derived from meta-hydroxybenzaldehyde provides compounds of Tables 1,3,5 of Formula II (wherein $R_1=R_2=H$). Alkylation of intermediate V, wherein $R_1=CH_3$ and $R_2=H$, derived from meta-hydroxybenzaldehyde provides compounds of Tables 7,8,9 of Formula II. Alkylation of intermediate V' derived from ortho-hydroxy-benzaldehdyde provides compounds of Tables 1,3,5 of Formula III (wherein $R_1=R_2=H$) Alkylation of intermediate V, wherein $R_1=CH_3$ and $R_2=H$, derived from ortho-hydroxybenzaldehdyde provides compounds of Tables 7,8,9 of Formula III. Alkylation of intermediate V' derived from para-hydroxybenzaldehdye provides compounds of Tables 1,3,5 of Formula IV (wherein $R_1=R_2=H$). Alkylation of intermediate V, wherein $R_1=CH_3$ and $R_2=H$, derived from para-hydroxybenzaldehdyde provides compounds of Tables 7,8,9 of Formula IV.

Compounds of formula VI where A is CH and V is O are prepared by the alkylation of V and V' with methyl E-α-(2-bromomethylphenyl)-β-methoxyacrylate in the presence of a base such as a metal hydride, preferably NaH, in an aprotic solvent such as N,N-dimethyl-formamide. Methyl E-α-(2-bromomethylphenyl)-β-methoxyacrylate, as a single E isomer, can be prepared in two steps from 2-methylphenylacetate as described previously in U.S. Pat. No. 4,914,128 columns 3–4.

Compounds of formula VI where A is N and V is oxygen are prepared from V and V' by the reaction with methyl E-2-(bromomethyl)phenylglyoxylate O-methyloxime in the presence of a base such as a metal hydride, preferably NaH, in an aprotic solvent such as N,N dimethylformamide. Methyl 2-(bromomethyl)phenylglyoxylate O-methyloxime can be prepared as described in U.S. Pat. Nos. 4,999,042, columns 17–18 and 5,157,144, columns 17–18. Methyl 2-(bromomethyl)phenylglyoxylate O-methyloxime is prepared from methyl 2-methylphenylacetate by treatment with an alkyl nitrite under basic conditions to provide after methylation, methyl 2-methylphenylglyoxalate O-methyl oxime which can also be prepared from methyl 2-methylphenylglyoxalate by treatment with 2-hydroxylamine hydrochloride and methylation or by treatment with methoxylamine hydrochloride.

An alternative synthetic route to examples when A is N and V is oxygen, is provided by the reaction of V and V' with methyl 2-(bromomethyl)phenylglyoxylate followed by reaction with methoxylamine HCl or hydroxylamine HCl followed by methylation.

The amminolysis of oximinoacetates to oximinoacetamides is described in U.S. Pat. Nos. 5,185,342, cols. 22, 48 and 57; 5,221,691, cols. 26–27, and 5,407,902, col. 8. Compounds of formula VI where A is N and V is O are treated with 40% aqueous methylamine in methanol to provide compounds of formula VI where V is NH. Alternatively compounds of formula VI can be prepared from compounds of formula V by coupling with N-methyl E-2-methoxyimino-2-[2-(bromomethyl)phenyl]acetamide in the presence of a base such as a metal hydride, preferably NaH, in an aprotic solvent such as dimethyl formide (DMF). The preparation of N-methyl E-2-methoxyimino-2-[2-(bromomethyl)phenyl]acetamide is described in U.S. Pat. No. 5,387,714, col. 13.

Scheme B describes the preparation of compounds of the formula (I) where n=1 and m=0. The α,β unsaturated compounds (VII) can be prepared by conventional condensation techniques as is described in Scheme A. A benzaldehyde is condensed with a hydroxyphenylketone, (OH)ArCOCH$_2$R$_2$, which when R$_2$=H a methyl ketone, provides the unsaturated intermediate VII'.

Scheme B:

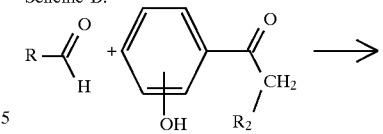

when R$_2$ = H

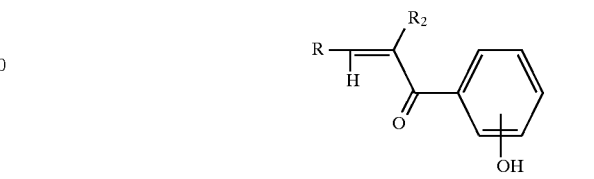

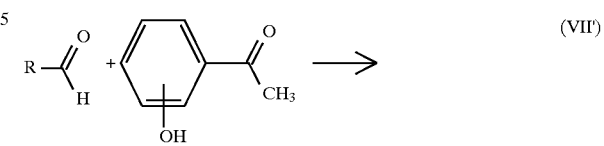

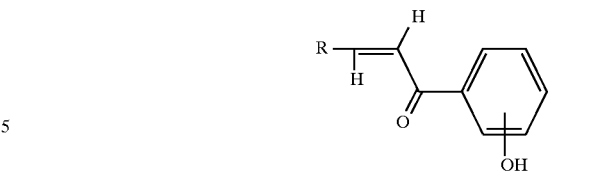

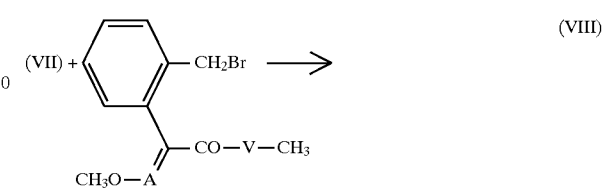

V = O, NH
A = CH, N

Scheme B:
-continued

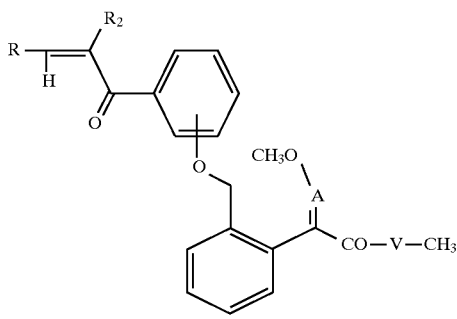

Substituted hydroxyphenylketones such as ortho, meta or para-hydroxyacetophenone provides three regioisomeric intermediates VII' wherein $R_2$=H. A variety of reaction conditions can be employed to prepare the enones VII and VII' and are described in *Organic Reactions,* Volume 16, pp. 69–85. For example, to the hydroxyphenylketone and aldehyde in a hydroxylic solvent, such as ethanol, is added a hydroxide base such as barium, sodium or potassium hydroxide. The reaction mixture is stirred at reflux when using barium hydroxide while with sodium or potassium hydroxide the reaction is conducted from 0° C. to 35° C. preferably at ambient temperature. After neutralization the product is isolated by conventional methods.

Compounds of formula VIII are prepared by the alkylation of intermediate VII and VII' with the appropriately substituted benzyl bromides. Alkylation of intermediate VII' derived from meta-hydroxyacetophenone provides compounds of Tables 2,4,6 of Formula II (wherein $R_1$=$R_2$=H). Alkylation of intermediate VII, wherein $R_2$=$CH_3$, derived from meta-hydroxypropiophenone provides compounds of Tables 10,11,12 of Formula II. Alkylation of intermediate VII' derived from ortho-hydroxyacetophenone provides compounds of Tables 2,4,6 of Formula III (wherein R=$R_2$=H). Alkylation of intermediate VII, wherein $R_2$=$CH_3$, derived from ortho-hydroxypropiophenone provides compounds of Tables 10,11,12 of Formula III. Alkylation of intermediate VII' derived from para-hydroxyacetophenone provides compounds of Tables 2,4,6 of Formula IV (wherein $R_1$=$R_2$=H). Alkylation of intermediate VII, wherein $R_2$=$CH_3$, derived from para-hydroxypropiophenone provides compounds of Tables 10,11,12 of Formula IV.

The following examples are illustrative of the present invention.

EXAMPLE 1

Methyl 3-methoxy-2-[2-(3-((3'-(3"-methoxyphenyl)-3'-oxo-prop-1'-enyl)phenoxymethyl) phenyl]propenoate (Compound 1.20, Table 1)

To a 20 ml vial equipped with magnetic stirring bar was charged 0.15 g (0.00197 moles) of 3'-methoxy-3-hydroxychalcone, 0.13 g (0.00197 moles) of powdered 86% potassium hydroxide, and 10 ml of dry N, N-dimethylformamide. To this solution was added 0.51 g (0.00197 moles) of methyl α-(2-(bromomethyl)phenyl)-β-methoxyacrylate in one portion. The vial was capped and the reaction was stirred overnight at ambient temperature. The reaction mixture was then poured into 100 mls of water and extracted with 2×100 mls of ethyl ether. The organic extract was then washed with 100 ml of water, and 100 ml of saturated aqueous sodium chloride solution. The ether extract was dried over anhydrous magnesium sulfate, filtered, and concentrated under reduced pressure with a rotary evaporator at 45° C. to afford 0.9 g of crude product as a dark red oil. This material was chromatographed on a mixed bed of neutral alumina and silica gel with 50% ethyl acetate, 50% hexane. The pure fractions were combined to yield 0.6 g (66% yield) of methyl 3-methoxy-2-[2-(3-((3'-(3"-methoxyphenyl)-3'-oxo-prop-1'-enyl)) phenoxymethyl) phenyl]propenoate as a viscous pale yellow oil.

H-NMR (200 MHz, $CDCl_3$): 3.7(s,3H); 3.8(s,3H); 3.9(s, 3H); 5.1(s,2H); 7.0(m,1H); 7.1–7.6(m,12H); 7.7(s,1H); 7.8 (d,1H)

EXAMPLE 2

Preparation of 3'-methoxy-3-hydroxychalcone (Used in the Preparation of the Compound 1.20 in Example 1)

To a 250 ml round bottom flask equipped with magnetic stirrer and side arm addition funnel was charged 6.0 g (0.04 moles) of 3'-methoxyacetophenone and 50 ml of absolute ethanol. 3-hydroxybenzaldehyde (4.9 g, 0.04 moles) and 3.2 g of 86% potassium hydroxide (0.05 moles) were dissolved in 50 ml of water and added dropwise to the stirring solution of 3'-methoxyacetophenone, at room temperature. The reaction was stirred at ambient temperature overnight, then poured into 250 mls of water, and acidified to pH 2 with 1N aqueous hydrochloric acid. A yellow precipitate formed, which was collected by vacuum filtration, and washed with water, and dried in vacuuo at 40° C. overnight A total of 8.7 g (85% yield) of product, 3'-methoxy-3-hydroxychalcone, was isolated as a tan solid. MP=74°–77° C.

H-NMR (200 MHz, $CDCl_3$): 3.8(s,3H); 6.4(bs,1H); 6.9 (m,1H); 7.1–7.7(m,8H); 7.8(d,1H)

EXAMPLE 3

Preparation of Methyl 3-methoxy-2-[2-(3'-(3"-phenyl-1'-oxo-prop-3'-en-yl)phenoxymethyl)phenyl] propenoate (Compound 2.01, Table 2)

3'-hydroxychalcone was coupled with methyl α-(2-(bromomethyl)phenyl)-β-methoxy acrylate using the procedure of Example 1 and 1.0 g (100% yield) of product was isolated as an oil.

H-NMR (200 MHz, $CDCl_3$): 3.7(s,3H); 3.85(s,3H); 5.1 (s,2H); 7.1(m,3H); 7.1–7.6(m,11H); 7.6(s,1H); 7.8(d,1H)

EXAMPLE 4

Preparation of 3'-hydroxychalcone

To a 250 ml round bottom flask equipped with a magnetic stirrer and reflux condensor, was charged 2.7 g (0.02 moles) of 3'-hydroxyacetophenone, 2.1 g (0.02 moles) of benzaldehyde, 2.0 g (0.011 moles) of barium hydroxide, monohydrate, and 20 ml of absolute ethanol. The reaction was refluxed for a total of 2.5 hours, after which it became thick and difficult to stir. Upon cooling, the resulting solid was dissolved in 100 mls of 1N aqueous hydrochloric acid, and another solid was observed to precipitate from solution. The solid was collected by vacuum filtration, and washed with 100 mls of water, then 100 mls of hexane and dried in vacuo at 40° C. for 24 hours. 4.2 g (93% yield) of 3'-hydroxychalcone was isolated as a tan solid. MP=143°–147° C.

EXAMPLE 5

Proton NMR data (200 MHz) are provided for the compounds of Tables 1 to 12.

TABLE 13

| Compound # | |
|---|---|
| 1.01 | 3.7(s, 3H); 3.9(s, 3H); 5.1(s, 2H); 7.0(d, 1H); 7.1–7.8(m, 13H); 8.0(d, 2H) |
| 1.02 | 3.7(s, 3H); 3.9(s, 3H); 5.1(s, 2H); 7.0(m, 2H); 7.1–7.6(m, 8H); 7.7(s, 1H); 7.8(m, 3H); 8.1(d, 2H) |
| 1.03 | 3.7(s, 3H); 3.9(s, 3H); 5.0(s, 2H); 6.9(d, 2H); 7.1–7.6(m, 11H); 7.8(d, 1H); 8.0(d, 2H) |
| 1.04 | 3.7(s, 3H); 3.9(s, 3H); 5.0(s, 2H); 7.0(d, 1H); 7.1–7.5(m, 12H); 7.6(s, 1H); 7.7(s, 1H) |
| 1.05 | 3.7(s, 3H); 3.9(s, 3H); 5.1(s, 2H); 6.8(d, 1H); 6.9(m, 1H); 7.1–7.6(m, 12H); 7.7(s, 1H); 8.0(d, 1H) |
| 1.07 | 3.7(s, 3H); 3.9(s, 3H); 5.1(s, 2H); 7.0(d, 1H); 7.1–7.6(m, 10H); 7.7(s, 1H); 7.8(d, 1H); 7.9(d, 1H); 8.0(s, 1H) |
| 1.10 | 3.7(s, 3H); 3.9(s, 3H); 5.1(s, 2H); 7.0(m, 1H); 7.1–7.6(m, 11H); 7.6(s, 1H); 7.9(d, 2H) |
| 1.15 | 3.6(s, 3H); 3.8(s, 3H); 5.0(s, 2H); 7.0(m, 2H); 7.1–7.6(m, 8H); 7.6(s, 1H); 7.7(m, 1H); 7.8(d, 1H); 7.9(d, 2H) |
| 1.18 | 3.8(s, 3H); 3.9(s, 3H); 5.1(s, 2H); 7.0(m, 1H); 7.1–7.6(m, 10H); 7.7(s, 1H); 7.8(d, 1H); 8.1(m, 2H) |
| 1.19 | 3.7(s, 3H); 3.8(s, 3H); 3.9(s, 3H); 5.0(s, 2H); 6.9–7.5(m, 10H); 7.6(s, 1H); 7.7(m, 2H) |
| 1.20 | 3.7(s, 3H); 3.8(s, 3H); 3.9(s, 3H); 5.1(s, 2H); 7.0(m, 1H); 7.1–7.6(m, 12H); 7.7(s, 1H); 7.8(d, 1H) |
| 1.21 | 3.7(s, 3H); 3.8(s, 3H); 3.9(s, 3H); 5.1(s, 2H); 7.0(m, 3H); 7.1–7.5(m, 8H); 7.6(s, 1H); 7.7(d, 1H); 8.1(d, 2H) |
| 1.22 | 2.5(s, 3H); 3.7(s, 3H); 3.9(s, 3H); 5.0(s, 2H); 6.9(d, 2H); 7.0–7.6(m, 12H); 7.7(s, 1H) |
| 1.23 | 2.4(s, 3H); 3.7(s, 3H); 3.9(s, 3H); 5.0(s, 2H); 6.9(d, 2H); 7.0–7.5(m, 10H); 7.6(s, 1H); 7.8(m, 2H) |
| 1.24 | 2.5(s, 3H); 3.65(s, 3H); 3.9(s, 3H); 5.0(s, 2H); 7.0(d, 2H); 7.1–7.5(m, 10H); 7.6(s, 1H); 8.0(m, 2H) |
| 1.27 | 3.6(s, 3H); 3.9(s, 3H); 5.0(s, 2H); 7.0(m, 1H); 7.1–7.5(m, 8H); 7.6(s, 1H); 7.7(m, 3H); 8.1(d, 2H) |
| 1.36 | 2.4(s, 3H); 3.7(s, 3H); 3.9(s, 3H); 5.0(s, 2H); 6.7(d, 1H); 6.9–7.5(m, 5H); 7.6(m, 2H); 7.7(s, 1H) |
| 1.38 | 1.0(t, 3H); 1.7(q, 2H); 2.7(t, 3H); 3.7(s, 3H); 3.9(s, 3H); 5.0(s, 2H); 6.7(d, 1H); 7.0(dd, 1H); 7.1–7.6(m, 8H); 7.7(s, 1H) |
| 1.39 | 1.2(d, 6H); 3.0(m, 1H); 3.7(s, 3H); 3.9(s, 3H); 5.1(s, 2H); 6.8(d, 1H); 6.9(m, 1H); 7.0–7.5(m, 6H); 7.6(m, 3H) |
| 1.41 | 0.9(t, 3H); 1.3(m, 6H); 1.7(m, 2H); 2.7(t, 3H); 3.8(s, 3H); 3.9(s, 3H); 5.1(s, 2H); 6.7(d, 1H); 6.9(m, 1H); 7.0–7.5(m, 7H); 7.55(d, 1H); 7.6(s, 1H) |
| 1.43 | 1.3(s, 9H); 3.7(s, 3H); 3.9(s, 3H); 5.0(s, 2H); 6.9(m, 1H); 7.1–7.6(m, 7H); 7.6(s, 1H); 7.7(m, 2H) |
| 1.52 | 1.0(m, 2H); 1.2(m, 2H); 2.2(m, 1H); 3.7(s, 3H); 3.8(s, 3H); 5.0(s, 2H); 6.8(d, 1H); 6.9(m, 1H); 7.0–7.5(m, 7H); 7.6(d, 1H); 7.65(s, 1H) |
| 1.59 | 3.7(s, 3H); 3.9(s, 3H); 5.0(s, 2H); 7.0(d, 1H); 7.1–7.6(m, 8H); 7.7(s, 1H); 7.8(m, 2H); 8.2(m, 1H); 8.8(m, 1H) |
| 1.60 | 3.7(s, 3H); 3.9(s, 3H); 5.0(s, 2H); 7.0(d, 1H); 7.1–7.6(m, 9H); 7.7(s, 1H); 7.8(d, 1H); 8.3(m, 1H); 8.8(m, 1H), 9.3(m, 1H) |
| 1.63 | 3.7(s, 3H); 3.9(s, 3H); 5.1(s, 2H); 7.0(m, 1H); 7.1–7.5(m, 9H); 7.6(m, 1H); 7.7(s, 1H); 7.8(m, 1H); 7.9(m, 1H) |
| 1.65 | 3.7(s, 3H); 3.9(s, 3H); 5.1(s, 2H); 7.0(m, 1H); 7.1–7.4(m, 6H); 7.6(m, 2H); 7.7(s, 1H); 7.8(d, 2H); 7.9–8.2(m, 5H); 8.5(s, 1H) |
| 2.01 | 3.7(s, 3H); 3.85(s, 3H); 5.1(s, 2H); 7.1(m, 3H); 7.1–7.6(m, 11H); 7.6(s, 1H); 7.8(d, 1H) |
| 2.02 | 3.7(s, 3H); 3.9(s, 3H); 5.1(s, 2H); 7.0(dd, 2H); 7.1–7.6(m, 11H); 7.6(s, 1H); 7.8(m, 2H) |
| 2.03 | 3.7(s, 3H); 3.9(s, 3H); 5.1(s, 2H); 7.0(d, 2H); 7.1–7.6(m, 8H); 7.6(s, 1H); 7.7–7.8(m, 3H); 8.0(d, 2H) |
| 2.10 | 3.7(s, 3H); 3.9(s, 3H); 5.0(s, 2H); 7.0–7.6(m, 14H); 7.6(s, 1H) |
| 2.12 | 3.7(s, 3H); 3.9(s, 3H); 5.0(s, 2H); 7.0(d, 2H); 7.1–7.6(m, 10H); 7.6(s, 1H); 7.8(d, 2H) |
| 3.01 | 3.8(s, 3H); 4.0(s, 3H); 5.0(s, 2H); 6.9(m, 2H); 7.1–7.6(m, 11H); 7.7(d, 1H); 8.0(m, 2H) |

TABLE 13-continued

| Compound # | |
|---|---|
| 5.01 | 2.9(d, 3H); 4.0(s, 3H); 5.0(s, 2H); 6.8(bs, 1H); 6.9(m, 1H); 7.1–7.6(m, 11H); 7.7(d, 1H); 8.0(m, 2H) |
| 7.10 | 2.2(s, 3H); 3.7(s, 3H); 3.9(s, 3H); 5.0(s, 2H); 6.9(m, 2H); 7.0–7.5(m, 9H); 7.6(s, 1H); 7.7(d, 2H) |

EXAMPLE 6

Numerous compounds of this invention were tested for fungicidal activity in vivo against the diseases described below. The compounds were dissolved in a 2:1:1 mixture of water, acetone and methanol (by volume), sprayed onto the plants, allowed to dry (one to two hours) and then the plants were inoculated with the fungus. Each test utilized control plants which were sprayed with the water, acetone and methanol mixture and inoculated with the fungus. The remainder of the technique of each of the tests is given below and the results for various compounds described herein by the Example number in Table 13 against the various fungi at a dose of 300 grams per hectare. The results are reported as percent disease control, compared to the control wherein) one hundred was rated as total disease control and zero was no disease control. The application of the fungi to the test plants was as follows:

Wheat Leaf Rust (WLR)

*Puccinia recondita* (f. sp. tritici ) was cultured on 7 day old wheat (cultivar Fielder) over a 14 day period in the greenhouse. Spores were collected from the leaves by settling on aluminum foil. The spores were cleaned by sieving through a 250 micron opening screen and stored or used fresh. Storage employed sealed bags in an Ultralow freezer. A spore suspension was prepared from dry uredia by adding 20 mg (9.5 million spores) per mL of Soltrol oil. The suspension was dispensed into gelatin capsules (0.7 mL capacity) which attach to the oil atomizers. One capsule is used per flat of twenty of the 2 inch square pots of 7 day old Fielder wheat. After waiting for at least 15 minutes for the oil to evaporate from the wheat leaves, the plants were placed in a dark mist chamber (18°–20° C. and 100% relative humidity) for 24 hours. The plants were then put in the greenhouse for the latent period and scored after 10 days for disease levels. For protective tests the plants are inoculated one day after spraying the plants with the fungicide compounds.

Wheat Leaf Blotch (SNW)

*Septorin nodorum* was maintained on Czapek-Dox V-8 juice agar plates in an incubator in the dark at 20° C. for 48 to 72 hours, then incubated at 20° C. with alternating perios do 12 hours of light and 12 hours of darkness. A water suspension of the spores was obtained by shaking the portion of the plate with fungal material in deionized water and filtering through cheesecloth. The spore-containing water suspension was diluted to a spore concentration of $3.0 \times 10^6$ spores per ml. The inoculum was dispersed by a DeVilbiss atomizer over one week old Fielder wheat plants which had been previously sprayed with the fungicide compound. The inoculated plants were placed in a humidity cabinet at 20° C. with alternating 12 hours of light and 12 hours of darkness for 96 hours. The inoculated seedlings were then moved to a controlled environment room at 20° C. for 8 days of incubation. Disease control values were recorded as percent control.

Wheat Powdery Mildew (WPM)

*Erysiphe graminis* (f. sp. tritici) was cultured on wheat seedlings in a controlled temperature room at 65° to 70° F. Mildew spores were shaken from the culture plants onto wheat seedlings which had been previously sprayed with the fungicide compound. The inoculated seedlings were kept in a controlled temperature room at 65° to 75° F. and subirrigated. The percent disease control was rated 8 to 10 days after the inoculation.

Cucumber Powdery Mildew (CPM)

*Sphaerotheca fulginea* was maintained on cucumber plants, cv. Bush Champion, in the greenhouse. Inoculum was prepared by washing the spores from the leaves with water which had 1 drop of Tween 80 per 100 ml. After shaking the plants, the inoculum was filtered through cheese cloth and misted onto the plants with a squirt bottle mister. The plants were then placed in the greenhouse for infection and incubation. The plants were scored seven days after inoculation. Disease control values were recorded as percent control.

Tomato Late Blight (TLB)

*Phytophthora infestans* was cultured on V8 juice plus $CaCO_3$ agar for three to four weeks. The spores were washed from the agar with water and dipsersed by DeVilbiss atomizer over the leaves of three week old Pixie tomato plants which had been sprayed previously with experimental fungicides. The inoculated plants were placed in a humidity cabinet at 20° C. for 24 hours for infection. The plants were then removed to a controlled environment room at 20° C. The plants were scored for disease control after five days.

Grape Downy Mildew (GDM)

*Plasmopara vticola* was maintained on leaves of live grape plants, cv. Delaware, in the controlled temperature chamber at 20° C. in humid air with moderate light intensity for 7 to 8 days. A water suspension of the spores from infested leaves was obtained and the spore concentration was adjusted to about $3 \times 10^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. Disease control values were recorded as percent control seven days after inoculation.

When tested against cucumber powdery mildew at a dose of 300 grams per hectare, Examples 1.10, 1.15, 1.18, 1.19, 1.24, 1.27, 1.36, 1.38, 1.43, 1.65, 2.12 and 7.10 exhibited 85% or better control.

When tested against septoria nodorum at a dose of 300 grams per hectare Examples 1.01, 1.03, 1.04, 1.10, 1.39, 1.43, 1.52, 1.59, 1.63, and 2.01, 3.01, and 5.01 exhibited 85% or better control.

When tested against wheat leaf rust at a dose of 300 grams per hectare Examples 1.01, 1.02, 1.03, 1.07, 1.10, 1.18, 1.19, 1.20, 1,21, 1.22, 1.23, 1.24, 1.27, 1.36, 1.39, 1.41, 1.43, 1.51, 1.59, 1.60, 1.63, 1.65, 2.01, 2.03, 2.12, 5.01 and 7.10 exhibited 90% or better control.

At 300 grams per hectare Examples 1.02, 1.03, 1.04, 1.10, 1.18, 1.18, 1.19, 1.21, 1.23, 1.36, 1.39, 1.41, 1.43, 1.65, 2.10 and 2.12 exhibited 75% or better control against wheat powdery mildew Also at 300 grams/hectare, Examples 1.01, 1.02, 1.03, 1.04, 1.05, 1.07, 1.10, 1.18, 1.19, 1.20, 1,21, 1.22, 1.23, 1.24, 1.27, 1.36, 1.39, 1.43, 1.59, 1.60, 1.63, 1.65, 2.01, 2.02, 2.03, 2.12, 3.01, 5.01 and 7.10 provided 95% or better control against grape downy mildew.

Also at 300 grams/hectare, Examples 1.01, 1.04, 1.05, 1.07, 1.10, 1.15, 1.18, 1.38, 1.39, 1.43, 1.52, 1.59, 2.01, 2.12 and 7.10 provided 90% or better control against tomato latre blight.

The compounds of this invention are useful as agricultural fungicides and, as such, can be applied to various loci such as the seed, the soil or the foliage.

The compounds of this invention can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15).

The compounds of this invention can be advantageously employed in various ways. Since these compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

EXAMPLE 7

Numerous compounds of this invention were tested for insecticidal activity in vivo against the insects described below. The following test method was used to evaluate compounds of the present invention for insectidal activity. The compound to be evaluated was dissolved in an appropriate solvent, usually a mix of acetone, methanol and water, and sprayed over three excised leaf disks using a flat fan nozzle. After spraying, the leaf disks were allowed to dry.

Two disks were infested with the leaf chewing insects (southern armyworm and Mexican bean beetle) and the third leaf disk was already infested with the two-spotted spider mite prior to spraying. The tested insect species were:

AW southern armyworm *Spodoptera eridamia*

BB Mexican bean beetle *Epilachna varivestis*

MTA two-spotted spider mite *Teranychus uricate* Observations as percent control were made by visual inspection 24–48 hours after spraying.

When tested against southern army worm at 600 grams/hectare Examples 1.43, and 7.10 provided 90% or better control.

When tested against Mexican bean beetle at 300 grams/hectare Examples 1.07, 1.10, 1.18, 1.21, 1.27, 1.38, 1.39, 1.41, 1.43, 1.65, 2.03; and 7.10 provided 90% or better control.

When tested against two-spotted spider mite at 300 grams/hectare Examples 1.38 and 2.03 provided 90% or better control.

The compositions and compounds of this invention can be applied directly to the locus to be protected, as for example, the area around or upon plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.

Compositions and formulations according to the present invention may also include known pesticidal compounds. This expands the spectrum of activity of the composition. Suitable insecticides known in the art include those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier is meant any substance which can be used to dissolve, disperse of diffuse the active ingredient in the composition without impairing the active ingredients effectiveness and which by itself has no significant detrimental effect on the soil, equipment, desirable plants, or agronomic enviornment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a pyridazinone, 45 parts of a synthetic precipitated hydrated silicon dioxide, such as that sold under the trademark Hi-SilR, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7.

Dusts are prepared by mixing the compounds of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habitat at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:

1. A compound having the structure

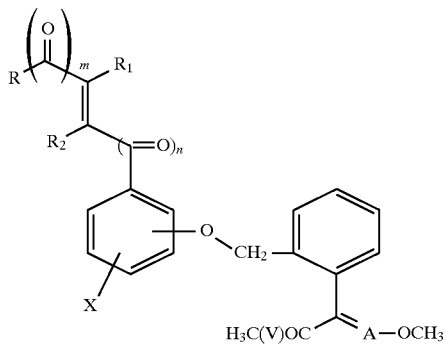

(I)

wherein A is N or CH; V is O or NH;
m and n are integers 0 and 1 provided that m+n is 1;
X is independently selected from the group consisting of hydrogen, halo, $(C_1-C_4)$alkyl, and $(C_1-C_4)$alkoxy;
R is independently selected from the group consisting of $(C_1-C_{12})$alkyl, halo$(C_1-C_{12})$alkyl, $(C_2-C_8)$alkenyl, $(C_2-C_8)$alkynyl, $(C_1-C_{12})$alkoxy$(C_1-C_{12})$alkyl, $(C_3-C_7)$cycloalkyl, $(C_3-C_7)$cycloalkyl$(C_1-C_4)$alkyl, aryl, aralkyl, and heterocyclic;
$R_1$ and $R_2$ are independently selected from the group consisting of hydrogen, $(C_1-C_6)$alkyl, halo$(C_1-C_{12})$alkyl, $(C_3-C_7)$cycloalkyl, $(C_3-C_7)$cycloalkyl$(C_1-C_4)$alkyl, cyano, carboxy$(C_1-C_4)$alkyl, and aryl; provided at least one of $R_1$ and $R_2$ is H.

2. The compound of claim 1 wherein A is CH.
3. The compound of claim 1 wherein A is N.
4. The compound of claim 2 wherein V is O.
5. The compound of claim 3 wherein V is O or NH.
6. The compounds of claim 4 where the moiety

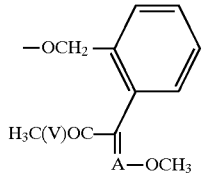

is meta to $(C=O)n-C(R_2)=C(R_1)-(C=O)_m$-R and R is selected from the group consisting of $(C_1-C_{12})$alkyl, halo $(C_1-C_{12})$alkyl, halosubstitutedphenyl, $(C_1-C_4)$alkyl substituted phenyl, and trihalosubstituted phenyl.

7. The compound of claim 6 wherein n=0 and m=1.
8. The compound of claim 7 wherein R is selected from the group consisting of $(C_1-C_6)$alkyl, halo$(C_1-C_4)$alkyl, 2-halophenyl, 3-halophenyl, 4-halophenyl, 2-$(C_1-C_4)$ alkylphenyl, 3-$(C_1-C_4)$alkylphenyl and 4-$(C_1-C_4)$ alkylphenyl.
9. The compound of claim 8 wherein R is selected from n-propyl, isopropyl, tert-butyl, n-butyl, n-hexyl, 4-fluorophenyl, 4-chlorophenyl and 4-trifluoromethylphenyl.
10. The compound of claim 5 where the moiety

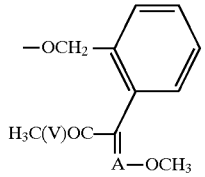

is meta to $(C=O)n-C(R)_2=C(R_1)-(C=O)_m$-R and R is selected from the group consisting of $(C_1-C_{12})$alkyl, halo $(C_1-C_{12})$alkyl, halosubstitutedphenyl, $(C_1-C_4)$alkyl substituted phenyl, and trihalosubstituted phenyl.

11. The compound of claim 10 wherein n=0 and m=1.
12. The compound of claim 11 wherein R is selected from the group consisting of $(C_1-C_6)$alkyl, halo$(C_1-C_4)$alkyl, 2-halophenyl, 3-halophenyl, 4-halophenyl, 2-$(C_1-C_4)$ alkylphenyl, 3-$(C_1-C_4)$alkylphenyl and 4-$(C_1-C_4)$ alkylphenyl.
13. The compound of claim 12 wherein R is selected from n-propyl, isopropyl, tert-butyl, n-butyl, n-hexyl, 4-fluorophenyl, 4-chlorophenyl and 4-trifluoromethylphenyl.
14. A fungicidal composition for controlling phytophathogenic fungi which comprises an agronomically acceptable carrier and the compound of claim 1 wherein the ratio of the carrier to the compound is 99:1 to 1:4.
15. The composition of claim 14 wherein the weight ratio of the agriculturally acceptable carrier to compound is 10:1 to 1:3.
16. A method for controlling phytophathogenic fungi which comprises applying to the seed, plant or soil the compound of claim 1 at a rate of from 0.005 to 50 kilograms per hectare.
17. The method of claim 16 wherein the compound of claim 1 is applied at the rate of from 0.025 to 10 kilograms per hectare.
18. A method for controlling insection an area which comprises applying to the area the compound of claim 1 at a rate of 0.005 to 10 kilograms per hectare.
19. The method of claim 18 wherein the compound is applied at a rate of 0.01 to 1 kilogram per hectare.

* * * * *